United States Patent [19]
Pleass et al.

[11] Patent Number: 5,229,849
[45] Date of Patent: Jul. 20, 1993

[54] LASER DOPPLER SPECTROMETER FOR THE STATISTICAL STUDY OF THE BEHAVIOR OF MICROSCOPIC ORGANISMS

[75] Inventors: C. M. Pleass, Sand Point, Id.; Bin Zheng; Charles S. Ih, both of Newark, Del.

[73] Assignee: University of Delaware, Newark, Del.

[21] Appl. No.: 821,413

[22] Filed: Jan. 15, 1992

Related U.S. Application Data

[63] Continuation-in-part of Ser. No. 651,402, Sep. 17, 1984, Pat. No. 5,108,907.

[51] Int. Cl.[5] .......................... C12Q 1/04; C12Q 1/22; G01P 3/36; H04N 7/18
[52] U.S. Cl. ..................................... 358/93; 356/28.5; 358/107; 382/6
[58] Field of Search .................. 358/93, 106, 107; 382/6; 356/28.5

[56] References Cited

U.S. PATENT DOCUMENTS

| | | | |
|---|---|---|---|
| 3,931,462 | 1/1976 | Exton | 358/107 |
| 4,121,247 | 10/1978 | Henry | 358/107 |
| 4,320,415 | 3/1982 | Jones | 358/107 |
| 4,338,024 | 7/1982 | Bolz | 382/6 |
| 4,519,087 | 5/1985 | Deindoerfer | 382/6 |
| 4,654,139 | 3/1987 | Baba | 358/101 |
| 4,972,258 | 11/1990 | Wolf | 358/93 |
| 5,003,611 | 3/1991 | Miyake | 382/6 |
| 5,108,907 | 4/1992 | Pleass et al. | 356/28.5 |

OTHER PUBLICATIONS

A. T. Cheung, "Quantitative Microscopy: A micro-image-analysis approach to characterize and quantitate biomotility", Engineering Science, Fluid Dynamics, World Publishing Co., 1990.
D. Z. Anderson, D. M. Lininger, Optical tracking novelty filter, Optics Letters, vol. 12, p. 123, 1987.
Y. Li, A. Kostrzewski, D. H. Kim, "Liquid crystal TV-based white light optical tracking novelty filter", Applied Optics, vol. 28, p. 4861, 1989.
N. George, S. G. Wang, D. L. Venable, "Pattern recognition using the ring-wedge detector and neural-network software," SPIE, vol. 1134, p. 96, 1989.
E. C. Tam, "Autonomous real-time object tracking with an adaptive joint transform correlator," Optical Engineering, vol. 29, p. 314, 1990.

Primary Examiner—Howard W. Britton
Attorney, Agent, or Firm—Connolly and Hutz

[57] ABSTRACT

An improved method and system of monitoring and identifying microbiota swimming in a fluid or moving across surfaces in a fluid provides a sensitive method for rapidly measuring very small changes in activity, and detecting and identifying individual microbes in relatively large volumes of fluid, even in the presence of detritus. The system comprises a laser station, a sample collector station, a picture taking station and a monitoring station.

33 Claims, 7 Drawing Sheets

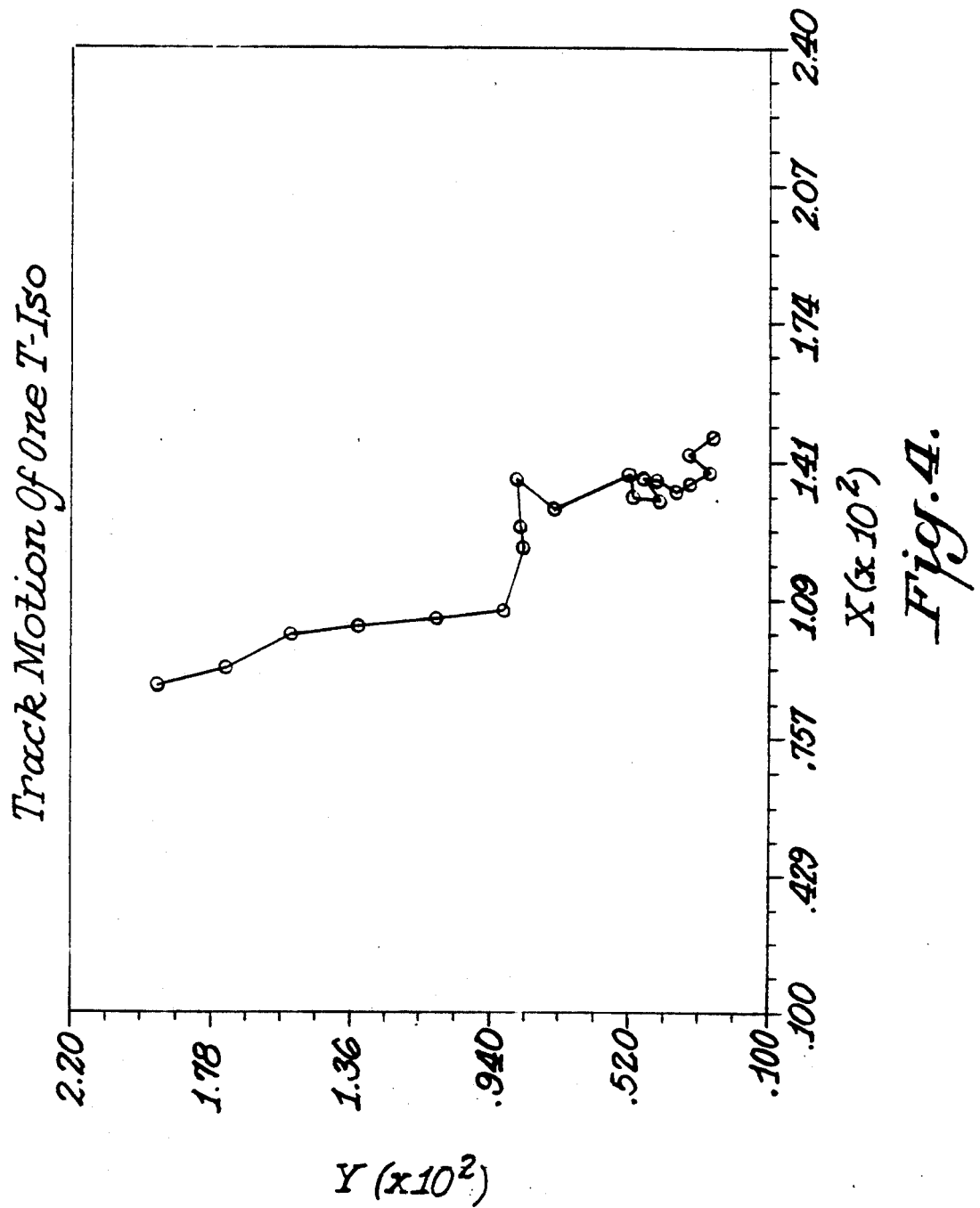

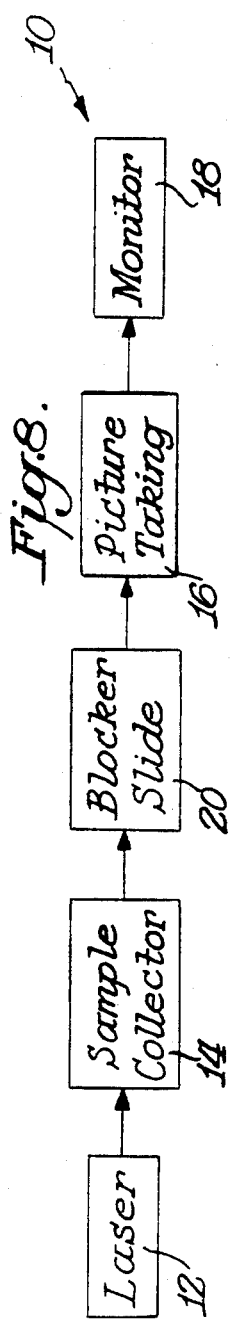
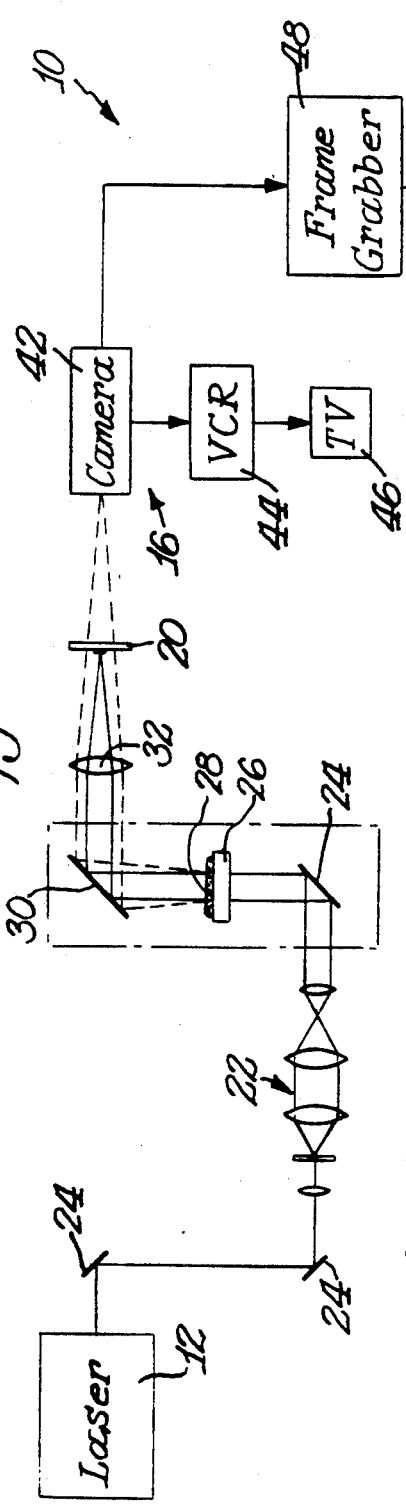

LASER DOPPLER SPECTROMETER FOR THE STATISTICAL STUDY OF THE BEHAVIOR OF MICROSCOPIC ORGANISMS

CROSS-REFERENCE TO RELATED APPLICATION

This application is a continuation-in-part of Ser. No. 06/651,402, filed Sep. 17, 1984 now U.S. Pat. No. 5,108,907.

BACKGROUND OF THE INVENTION

There has been a need to find microbes in relatively large volumes of fluid, observe the activity, and identify the species. Some of the microbes that can be monitored include giardia, salmonella, escherichia coli, isochrysis, to name a few. Such fluids are, but not limited to, waste water or blood. The prior art used a system of placing a fluid sample on a glass slide and then sandwiching the sample by placing another glass slide on top of the fluid and viewing the sample with a microscope. There are a number of problems with this technique. The samples would die for lack of adequate gas exchange shortly after placement of the second slide which necessitated an immediate monitoring. The sample was also restricted to a very small volume of fluid because the top slide would displace the sample. It was virtually impossible to observe all the different types of microbe activity in the fluid. In instances where the need was to ascertain the presence or absence of a few microbes in, for example, a sample drawn from a reservoir, the very small fluid volume made direct microscopic observation useless.

There have been articles written about tracking microbes. The closest reference is a paper written by A. T. Cheung, "Quantitative Microscopy: A micro-image-analysis approach to characterize and quantitate biomotility" published in Engineering Science, Fluid Dynamics, by World Publishing Company, 1990. The article describes an optical-digital system to track the motion of microbes. The system is based on a microscope, a video camera and a computer processing system. Because that system uses a microscope to extract information describing motility, it can not monitor and track the motion of microbes in their natural state and in real-time. The limitation of that system has been mentioned in the first paragraph. Other references that relate to the tracking but are not as relevant as the paper written by A. T. Cheung are:

(1) D. Z. Anderson, D. M. Lininger, Optical tracking novelty filter, Optics Letters, Vol. 12, p. 123, 1987.

(2) Y. Li, A. Kostrzewski, D. H. Kim, Liquid crystal TV-based white light optical tracking novelty filter, Applied Optics, Vol. 28, p. 4861, 1989.

(3) N. George, S. G. Wang, D. L. Venable, Pattern recognition using the ring-wedge detector and neural-network software, SPIE, Vol. 1134, p. 96, 1989.

(4) E. C. Tam, Autonomous real-time object tracking with an adaptive joint transform correlator, Optical Engineering, Vol. 29, p. 314, 1990.

A number of articles of interest dealing with this subject are in a text entitled "The Application of Laser Light Scattering to the Study of Biological Motion" edited by J. C. Ernshaw and M. W. Steer, copyright 1990, Plenum Publishing Corp. Several articles in this text deal with laser light measurements of motility of living cells and microorgansims, with particular reference being made to the article by J. S. Ernshaw entitled "Laser Doppler Velocimetry" which describes a differential laser doppler in which one of the beams was electronically down mixed to give effective frequency shifts as low as 10 kHz, and the article by J. P. Boon entitled "Motility of Living Cells and Microorganisms" which describes the effect of stimuli on the motility of cells.

SUMMARY OF INVENTION

A primary objective of this invention is to provide an improved method and system of monitoring and identifying microbiota swimming in a fluid and to provide a sensitive method for rapidly measuring very small changes in their concentration, species composition, motility and direction of movement.

Other parameters, such as the average size of the individuals, and the growth of the total number of organisms in suspension can also be monitored. The present invention can readily be applied to phytoplankton, zooplankton, bacteria or microecosystems containing a variety of suspended microscopic plants, animals, and detritus. The invention is useful in the area of bioremediative process control, ecology, medicine, cell biology, etc..

Another advantage of this invention is to allow the characterization of a sample that will retain its vigor for a long time period as compared to the time required for such characterization.

A further advantage of this invention is to provide a method which will allow rapid in situ determination of the characteristic biota in natural and man-made bodies of water.

A still further advantage of this invention is to provide a method for continuously monitoring bioremediation systems active in fluid environments.

Additional advantages of this invention are to provide a method of monitoring the vigor of microbes in the presence of large quantities of colloidal material such as natural detritus or industrial waste products.

BRIEF DESCRIPTION OF THE DRAWINGS

The invention will be described in greater detail in the following specification in conjunction with the accompanying drawings wherein:

FIG. 4 illustrates the digital record of the track of one t-Isochrysis cell which can be monitored by this invention;

FIG. 8 is a schematic block diagram of an apparatus incorporating the invention;

FIG. 9 is a more detailed schematic diagram of the system shown in FIG. 8;

FIG. 10 is a front view of the blocker slide of FIGS. 8-9;

FIG. 11 is a side view of the blocker slide shown in FIG. 10; and

DETAILED DESCRIPTION OF THE INVENTION

Figure 1A:
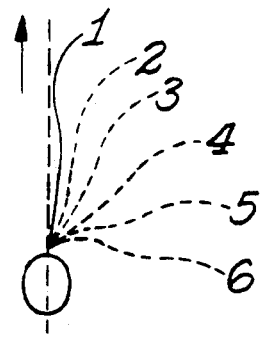
FIGS. 1A–1D illustrate patterns of flagellar movement in microscopic algae which can be monitored by this invention.
Figure 1B:
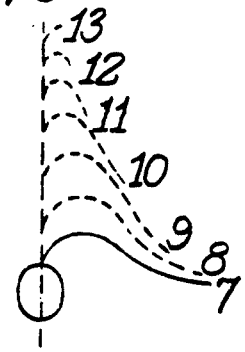
Figure 1C:
Figure 1D:
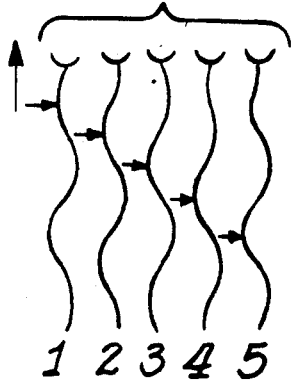
Figure 2A:
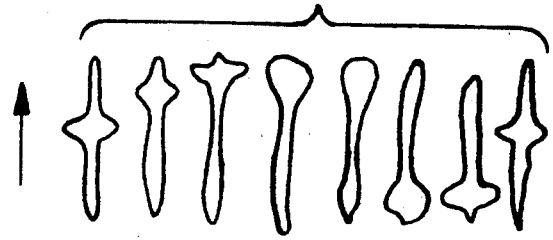
FIGS. 2A and B illustrate patterns of metabolic movements of another form of microbe which can be monitored by the invention.
Figure 2B:
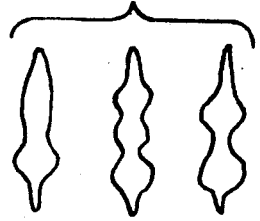

FIGS. 1A-1D show patterns of flagellar movement of algae, FIG. 1 showing "pull" type with FIG. 1A showing the power stroke and FIG. 1B showing the return stroke; FIG. 1C shows "propeller" type locomotion and FIG. 1D showing "undulatory" type motion, with a wave (arrow) running over the flagellum. Successive positions are numbered. In FIGS. 2A and 2B, metabolic movements of the microbe Euglena are shown, FIG. 2A showing a single wave running over the cells in the direction of the arrow and FIG. 2B shows two or three waves running simultaneously. These diagrammatic sketches are from the text "Algal Physiology and Biochemistry" University of California Press, 1974, Chapter 31 by W. Nultsch entitled "Movements". These forms of motions can be used to help identify the species.

Figure 3A:
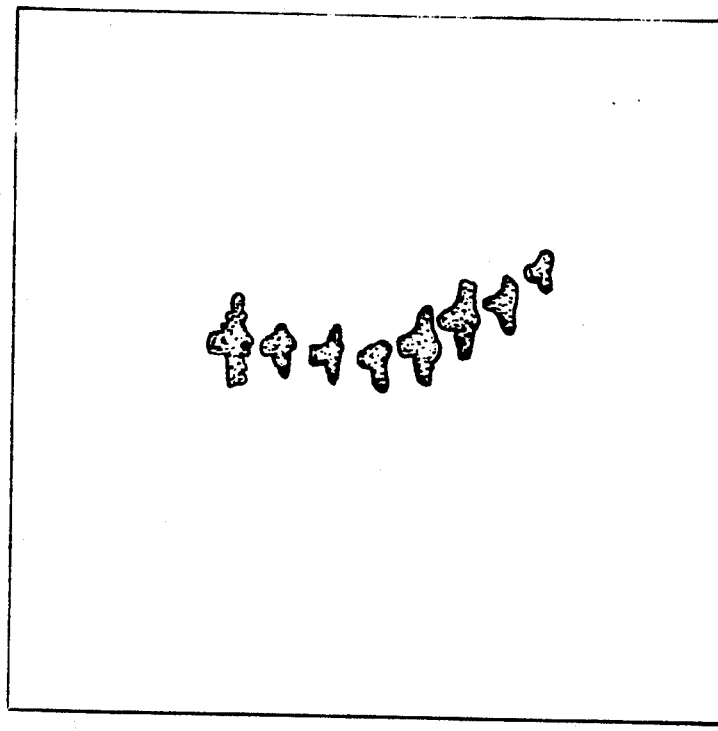
FIGS. 3A and B illustrate the track of an Isochrysis microbe which can be monitored by the invention.
Figure 3B:
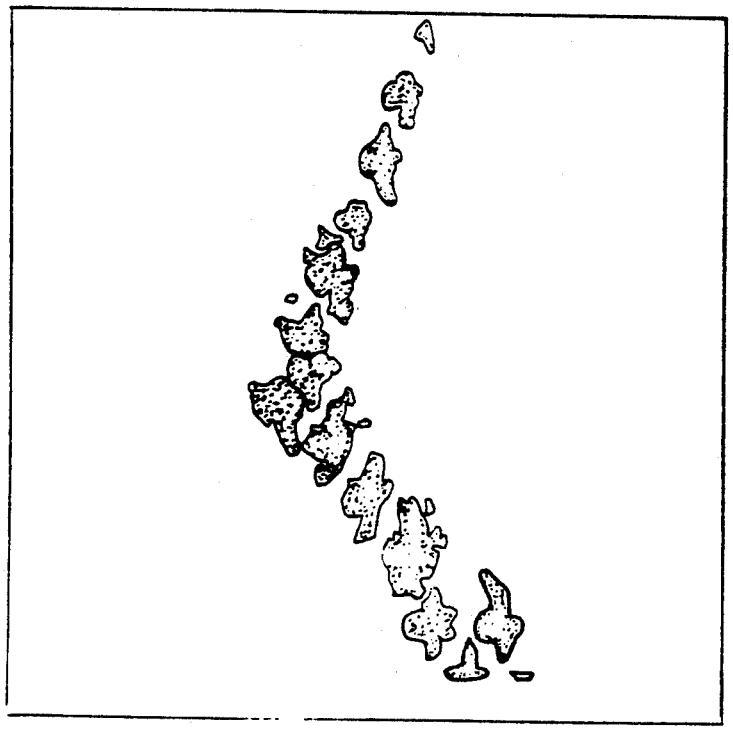

FIG. 3 illustrates the track of an Isochrysis microbe, represented by its diffraction pattern.

FIG. 4 illustrates the digital record of the track of one Isochrysis cell.

Figure 5:
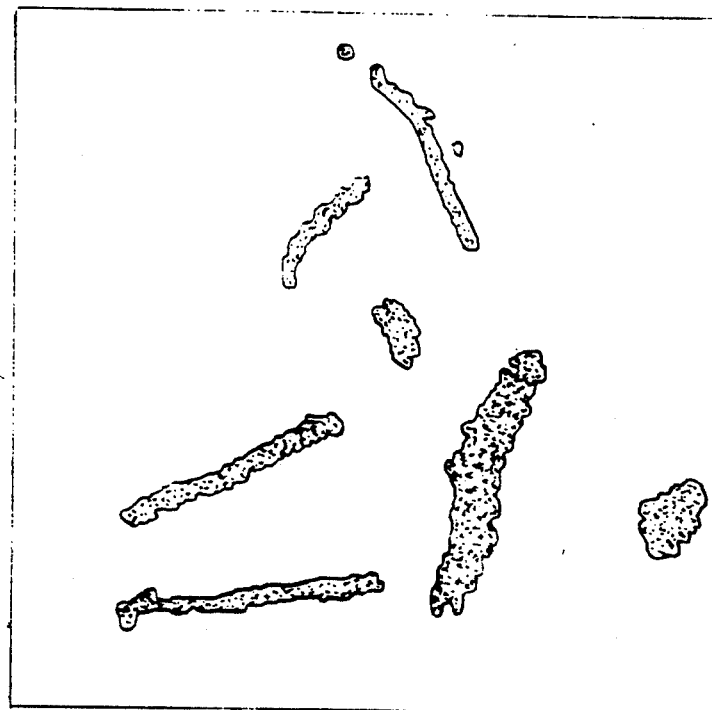
FIG. 5 illustrates the track of several Isochrysis microbes on one frame which can be monitored by the invention.

FIG. 5 illustrates an example of traces of several ISOs microbes tracked for 8 seconds. This picture is taken after the data-processing steps known as "erode" and "dilate" which improve the ratio of signal to background noise.

Figure 6:
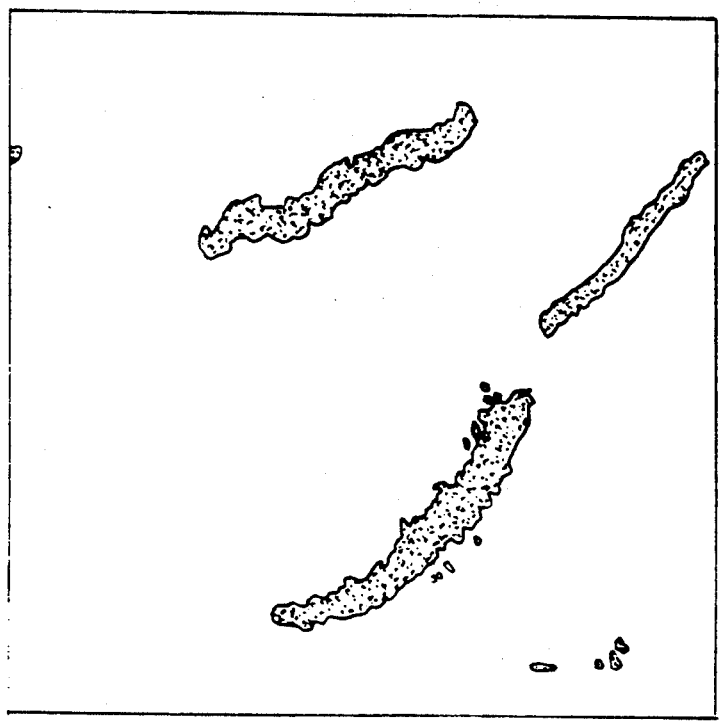
FIG. 6 illustrates the tracks of several Dunaliella microbes on one frame which can be monitored by the invention.

FIG. 6 illustrates several Dunaliella microbes to be tracked. This picture is taken after "erode".

Figure 7:
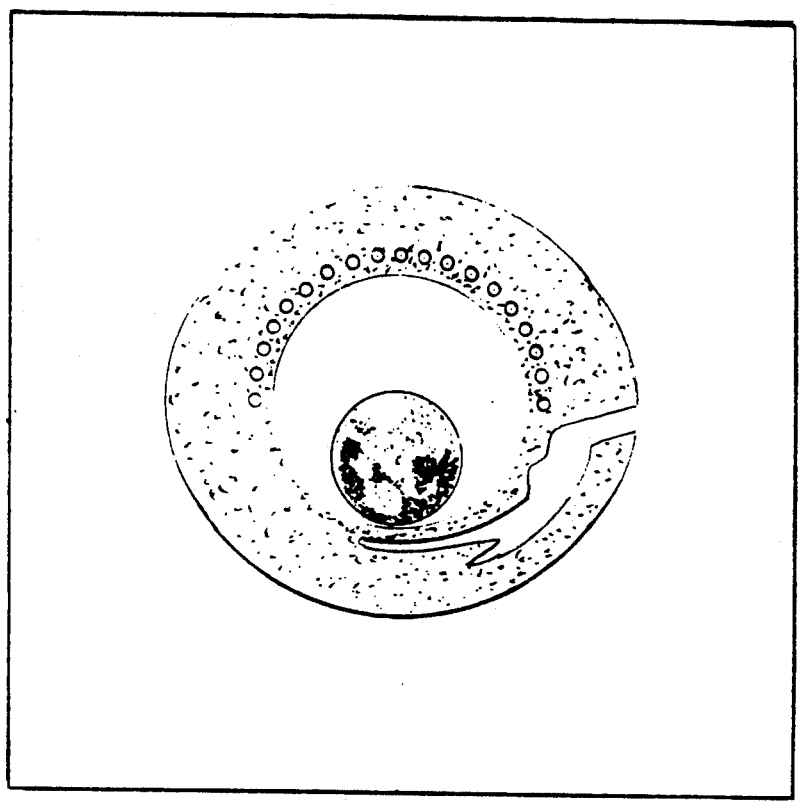
FIG. 7 illustrates the rotation of a microbe by using dynamic diffraction patterns.

FIG. 7 illustrates the rotation information of a microbe by using dynamic diffraction patterns.

Any microbe which moves can readily be monitored with the invention which is shown in schematic block diagram in FIG. 8. As shown therein, the system 10 of this invention comprises a laser station 12, a sample collector station 14, a picture taking station 16 and a monitoring station 18. If desired the system 10 may also include a blocking slide 20.

The invention may be broadly practiced by placing a fluid sample in the sample collection station 14. The laser station 12 has a laser for directing a laser beam at the fluid sample in the sample collector station 14 with the beam being diffracted by microbes on particulate in the sample. The picture taking station 16, has a picture taking means for taking a picture of the activity in the sample in accordance with the diffracted beam. The monitor station 18 is used for converting the picture to an analyzable record of the activity. A suitable type of monitoring may be used including those described in parent application Ser. No. 06/651,402, the details of which are incorporated herein by reference thereto. If desired the blocker slide may mask selected portions of the diffracted beam.

FIG. 9 illustrates a preferred practice of the invention. The laser station 12 has a laser such as but not limited to a helium neon laser. The laser emits a laser beam which travels to the sample collector station. The size and direction of the beam may be controlled by any suitable lens arrangement 22 and mirrors 24 between the laser station 12 and the sample collector station 14.

The sample collector station 14 has a sample collector which may be a transparent holder 26 such as glass or plastic for permitting light to pass. A fluid such as waste water, blood, etc. is placed on top of the holder. Unlike the prior art sandwich technique the top of the sample is left exposed. The sample collector is positioned so that the laser beams are emitted through the bottom of the holder and are within the volume of a fluid 28 carried in the holder 26. The sample collector or holder 26 may be housed in a suitable conventional closed system to control the environment such as temperature humidity and pressure as shown by the dotted lines around the sample collector 26 in FIG. 9.

Instead of having the sample in a closed container, the sample may flow through a transparent vessel and not remain in the vessel long enough to be deprived of respiration gases. The use of intermittent flow is a preferred way of presenting the sample to the laser beam. The flow would be stopped briefly for the period of the examination, making use of the fact that the method allows this examination to be done very rapidly. Then the flow would be restarted and stopped again after an appropriate time. The sample stream could move continuously through the sample volume. Unidirectional flow could be compensated during the analysis of frames from the camera.

After the beams pass through the sample collector, the beams travel through the blocker slide 20. Mirror 30 and lens 32 may be used to direct the diffracted beam to slide 20. The front view of the blocker slide 20 can be seen in FIG. 10 and FIG. 11. The blocker slide 20 is made from any transparent material, such as, but not limited to, glass or plastic. The function of the blocker slide 20 is only to block the central portion of laser beam (undiffracted laser beam) and has no influence on the diffracted laser beam. The center of the slide 20 has an opaque circle or dot 34 for blocking out the laser beams. The size of the opaque circle 34 controls the amount of beams passing through the slide 20. The bigger the circle the less the annular area of the beams that pass through. As shown in FIGS. 10-11 slide 20 may be detachably mounted against metal frame 36 by means of a retainer arm 38. Frame 36 in turn is attached to a base 40. Thus slides with different size opaque circles may readily replace one another.

Once the beams pass through the blocker station, the beams travel to the picture taking station 16. The picture taking station 16 has a camera 42. The camera can be, but is not limited to being, a video camera. The camera takes a picture of the activity in the sample in accordance with the diffracted laser light.

The data from the camera 42 is transmitted to the monitoring station 18. The monitoring station converts the picture to an analyzable record. The monitoring station can utilize various techniques depending on the needs of the user. One means can consist of a VCR 44 which can store the data on tape for a permanent record. In addition, a television 46 may be associated with the VCR 44 for an on line viewing of the microbiota. Any other suitable monitor could be used in place of a television for viewing.

Monitor station 18 may additionally or alternatively include a frame grabber 48, a computer 50 and a monitor 52. The frame grabber would convert the data and transmit it to the computer. The microbiota can be viewed on the monitor. Measurements can be taken and computed from the computer including size, velocity, etc.

This invention can also use a digital method to track the body rotation of a microbe via its dynamic diffraction patterns. Diffraction is another way to identify different microbe species. Every species has a different diffraction pattern. Tracking rotation of a microbe is much more difficult than tracking its position. In the position tracking, frames contained motion signals can be overlapped to form a final frame. When the tracking is finished, all the useful data is inside this final frame, can be processed later by a computer. However, in order to track rotation of a microbe in real time, data in the first frame must be taken out before the second frame comes in, and the data in the second frame must be extracted out before the third frame arrives, and so forth. Therefore, a system with a capability of parallel processing is required. (See FIG. 12)

Figure 12:
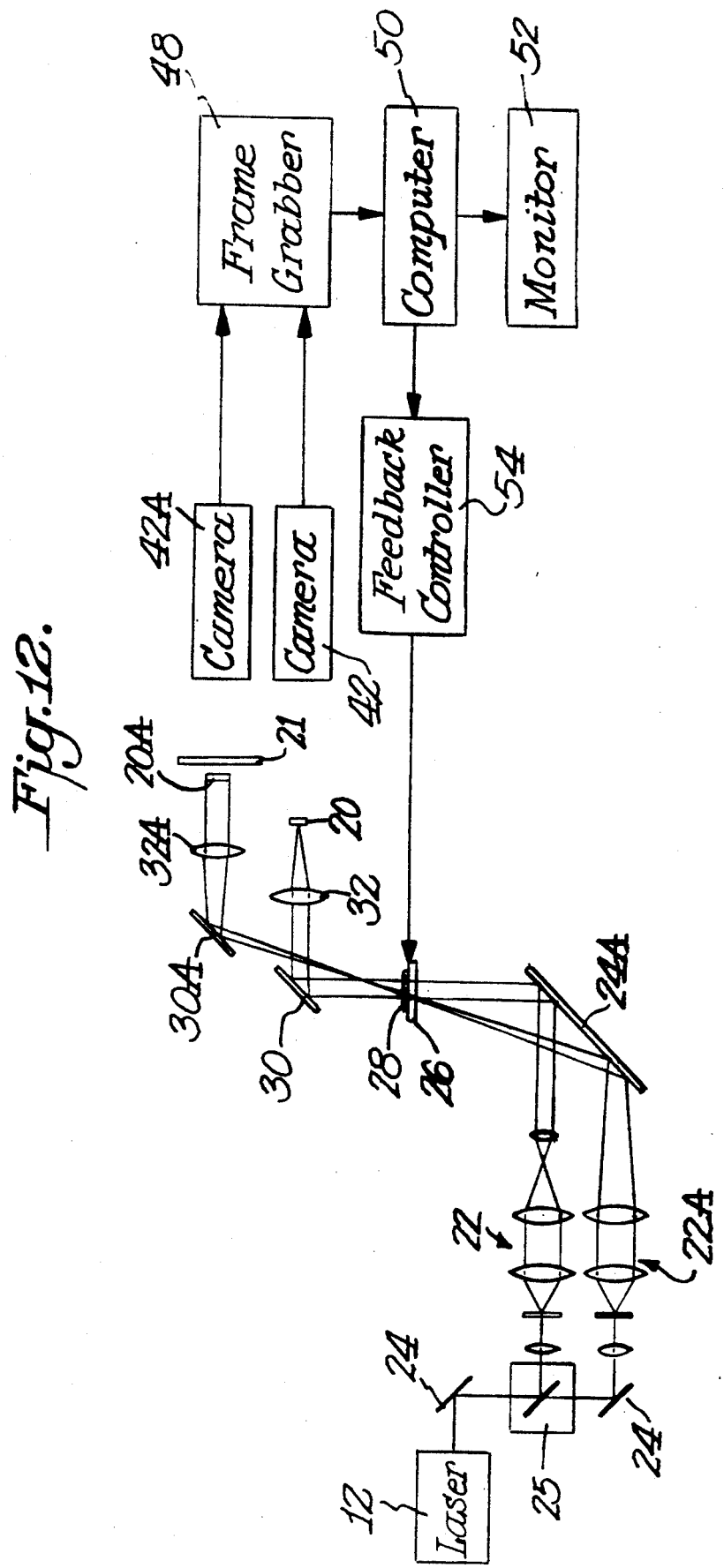
FIG. 12 is a detailed schematic diagram of the system using two laser beams for rotational measurements.

FIG. 12 is a modified system of FIG. 9 using two or more sets of laser beams. The modification includes a laser beam splitter 25 which splits the laser beam causing two sets of beams to travel through the sample 28. The second laser beam travels through similar components designated by the suffix "A". The laser beam can also travel through a filter 21. Typically, each frame of the frame grabber 48 contains 512×512 pixels. The on board memory of frame grabber 48 can only contain four such frames. If more than four frames are to be tracked, the data must be extracted and stored into a memory on a host computer. In order to track the rotation of a microbe, the first task here is how to reduce 512×512 digital numbers into a few numbers, but these numbers should contain enough information about rotation of a microbe, then it is very fast to transfer this data from the frame grabber to a computer.

As shown in FIG. 7, a semicircle is drawn. In this semicircle, 19 points are chosen equally-spacedly, the angle difference between any two points is 10°. As can be seen from FIG. 7, when diffraction patterns rotate, the "intensity" distribution along with semicircle is also rearranged, which reserves the important and useful information about rotation of a microbe. Thus, 512×512=262,144 numbers are heavily compressed into only 19 numbers. Transferring 19 numbers from frame grabber into a host computer will be much faster. In the video world, the "real-time" means 30 frames per second. This system has the capability of further approaching the destination of "real-time". Also more data can be sampled along this semicircle to improve the sensitivity of the system.

In a practical application of the invention, system 10 would be installed in a civic sewage disposal or waste water treatment plant. Samples of waste water would be monitored continuously and the information displayed in real time in the plant control room. Because of the increased life span of the microbes in the sample with the invention, it would not be necessary for the inspector to immediately view the sample. Additionally, because the invention produces a permanent analyzable record, the inspector can view and analyze the sample at the most convenient time. In addition, because the sample fluid is in a condition which more accurately reflects the condition of the fluid in its true environment, e.g. no top plate distorts gaseous exchange between the sample and the environment, what is being monitored is a reliable indication of actual conditions. The inspector would compare the sample being monitored with a standard which is representative of acceptable activities. If there is too great a deviation from the standard, the inspector would know that a problem was developing.

The sample techniques as described with waste water could be used for other fluids such as blood, beverages, and industrial process fluids such as those found in fermentation and bioremediation systems. In the inverse of the cases previously discussed, miniature versions of the equipment, which might, for example, be built inexpensively from semiconductor laser diodes, could be installed in fluid flow systems such as domestic drinking water lines, connected to alarms which would warn of unusually high bacteria levels.

Table 1 shows many different measurements of a diluted culture of Isochrysis as illustrated in FIG. 5. There were 7 microbes tracked. The sample time was 4 seconds.

Table 2 shows many different measurements of a diluted culture of Dunaliella as illustrated in FIG. 6. There were 3 microbes tracked. The sample time was 5 seconds.

Table 3 shows digital from the dynamic diffraction patterns from a Dunaliella cell which were taken as examples. The dynamic diffraction patterns associated with a given species can be continuously observed while tracking. If necessary an independent focussed laser beam can be used for this purpose. These patterns contain information about size, shape flagellation and motility and are unique to each specie and may be presented in analog or digital form.

Table 4 shows the results of tracking of microbes in sewage water. The microbes in an "oxidation ditch" in a sewage farm are composed of many different species. It is important for the operator of a plant to be able to see images (the dynamic diffraction patterns) which give confidence that all the normal members of the team are present and active.

TABLE 1

TRACKING MOTION OF MICROBES

Test Sample: Diluted Culture of ISO (2).
Sample Time in Second: 4

| Number | DX | DY | DD | AV | A0 | A1 | A2 | A3 | A4 |
|---|---|---|---|---|---|---|---|---|---|
| 1 | 70 | 124 | 143.19 | 36.93 | −63.95 | 6.129 | −0.0537 | 0.00000 | 0.0000 |
| 2 | 50 | 74 | 89.78 | 24.14 | 13.11 | 1.178 | 0.0000 | 0.00000 | 0.0000 |
| 3 | 11 | 42 | 44.47 | 6.83 | −14.33 | 1.000 | 0.0000 | 0.00000 | 0.0000 |
| 4 | 54 | 187 | 195.00 | 70.98 | 6154.70 | −231.539 | 2.8603 | −0.01157 | 0.0079 |
| 5 | 148 | 66 | 162.35 | 39.30 | 14.47 | 0.492 | 0.0000 | 0.00000 | 0.0000 |
| 6 | 31 | 54 | 62.89 | 22.72 | 81871.27 | −2042.292 | 16.9699 | −0.04695 | 0.0000 |
| 7 | 183 | 23 | 184.79 | 65.82 | 5.49 | 0.127 | 0.0000 | 0.00000 | 0.0000 |

| RD | D0 | T0 | D1 | T1 | D2 | T2 | D3 | T3 |
|---|---|---|---|---|---|---|---|---|
| 51.58 | 7.800 | 0.000 | 11.031 | −45.000 | 14.062 | −56.310 | 7.800 | 0.000 |
| 57.92 | 7.800 | 0.000 | 7.800 | 0.000 | 11.031 | 45.000 | 7.800 | 0.000 |
| 20.00 | 7.800 | 0.000 | 7.800 | 0.000 | 11.700 | 0.000 | 0.000 | 0.000 |
| 454.19 | 17.441 | 63.435 | 8.721 | 26.565 | 11.700 | 0.000 | 11.031 | 45.000 |

TABLE 1-continued

TRACKING MOTION OF MICROBES

| 13.77 | 11.700 | 0.000 | 14.062 | 33.690 | 21.002 | 21.801 | 24.666 | 18.435 |
|---|---|---|---|---|---|---|---|---|
| 109.73 | 19.500 | 0.000 | 11.031 | 45.000 | 8.721 | 26.565 | 7.800 | 0.000 |
| 10.45 | 11.700 | 0.000 | 24.666 | 18.435 | 68.111 | 13.241 | 27.300 | 0.000 |

| D4 | T4 | D5 | T5 | D6 | T6 | D7 | T7 | D8 |
|---|---|---|---|---|---|---|---|---|
| 11.031 | −45.000 | 11.700 | 0.000 | 14.062 | −56.310 | 7.800 | 0.000 | 14.062 |
| 14.062 | 56.310 | 8.721 | 26.565 | 5.515 | 45.000 | 11.031 | 45.000 | 8.721 |
| 0.000 | 0.000 | 0.000 | 0.000 | 0.000 | 0.000 | 0.000 | 0.000 | 0.000 |
| 11.700 | 0.000 | 7.800 | 0.000 | 11.700 | 0.000 | 11.700 | 0.000 | 84.009 |
| 14.062 | 33.690 | 8.721 | 26.565 | 14.062 | 33.690 | 17.441 | 26.565 | 14.062 |
| 8.721 | −276.565 | 19.500 | −36.870 | 7.800 | 0.000 | 7.800 | 0.000 | 0.000 |
| 11.700 | 0.000 | 42.004 | −21.801 | 11.031 | 0.000 | 66.757 | 0.000 | 0.000 |

| T8 | D9 | T9 | D10 | T10 | D11 | T11 | D12 | T12 |
|---|---|---|---|---|---|---|---|---|
| −56.310 | 12.333 | −71.565 | 19.500 | −36.870 | 16.546 | −45.000 | 0.000 | 0.000 |
| 26,565 | 14.062 | 56.310 | 0.000 | 0.000 | 0.000 | 0.000 | 0.000 | 0.000 |
| 0.000 | 0.000 | 0.000 | 0.000 | 0.000 | 0.000 | 0.000 | 0.000 | 0.000 |
| 68.199 | 47.446 | 80.538 | 11.700 | 0.000 | 24.666 | 71.565 | 8.721 | 26.565 |
| 33.690 | 17.441 | 26.565 | 0.000 | 0.000 | 0.000 | 0.000 | 0.000 | 0.000 |
| 0.000 | 0.000 | 0.000 | 0.000 | 0.000 | 0.000 | 0.000 | 0.000 | 0.000 |
| 0.000 | 0.000 | 0.000 | 0.000 | 0.000 | 0.000 | 0.000 | 0.000 | 0.000 |

Notes:
Number - represents number of microbes to be tracked.
DX,DY - maximum position change in X and Y direction (in micron).
DD - maximum linear position change (in micron).
AV - average velocity during sample period (micron/sec).
A0 to A4 - zero to forth order coefficient of motion trace equation.
RD - mean error of the least square curve fitting.
D0 to D12 - moving distance at each subsection during ST (in micron).
T0 to D12 - moving direction (arctan) of each subsection (in angle).

TABLE 2

TRACKING MOTION OF MICROBES

Test Sample: Dilute Culture of Dunaliella (1).
Sample Time in Second: 5

| Number | DX | DY | DD | AV | A0 | A1 | A2 | A3 | A4 |
|---|---|---|---|---|---|---|---|---|---|
| 1 | 206 | 97 | 228.54 | 50.31 | 57.20 | 0.536 | −0.0004 | 0.00000 | 0.0000 |
| 2 | 109 | 132 | 171.78 | 33.46 | −46.32 | 1.119 | 0.0000 | 0.00000 | 0.0000 |
| 3 | 202 | 136 | 244.46 | 52.13 | 49.13 | −1.732 | 0.0185 | 0.00000 | 0.0000 |

| RD | D0 | T0 | D1 | T1 | D2 | T2 | D3 | T3 |
|---|---|---|---|---|---|---|---|---|
| 100.36 | 11.700 | 0.000 | 11.700 | 0.000 | 11.031 | 45.000 | 11.700 | 0.000 |
| 34.83 | 22.741 | 59.036 | 16.546 | 45.000 | 19.500 | 53.130 | 22.741 | 59.036 |
| 48.88 | 23.400 | 0.000 | 27.300 | 0.000 | 36.999 | 18.435 | 19.500 | 36.870 |

| D4 | T4 | D5 | T5 | D6 | T6 | D7 | T7 | D8 |
|---|---|---|---|---|---|---|---|---|
| 11.031 | 45.000 | 17.441 | 26.565 | 14.062 | 33.690 | 57.583 | 28.301 | 19.886 |
| 22.062 | 45.000 | 16.546 | 45.000 | 14.062 | 33.690 | 16.546 | 45.000 | 16.546 |
| 19.500 | 36.870 | 14.062 | 56.310 | 27.577 | 45.000 | 33.549 | 54.462 | 27.577 |

| T8 | D9 | T9 | D10 | T10 | D11 | T11 | D12 | T12 |
|---|---|---|---|---|---|---|---|---|
| −11.310 | 15.600 | 0.000 | 19.500 | 0.000 | 27.577 | 45.000 | 11.031 | 45.000 |
| 45.000 | 0.000 | 0.000 | 0.000 | 0.000 | 0.000 | 0.000 | 0.000 | 0.000 |
| 45.000 | 11.700 | 0.000 | 19.500 | 36.870 | 0.000 | 0.000 | 0.000 | 0.000 |

Notes:
Number - represents number of microbes to be tracked.
DX,DY - maximum position change in X and Y direction (in micron).
DD - maximum linear position change (in micron).
AV - average velocity during sample period (micron/sec).
A0 to A4 - zero to forth order coefficient of motion trace equation.
RD - mean error of the least square curve fitting.
D0 to D12 - moving distance at each subsection during ST (in micron).
T0 to T12 - moving direction (arctan) of each subsection (in angle).

TABLE 3

Tracking Rotation of a Microbe from its Dynamic Diffraction Pattern

Tested Microbe: Dunaliella Teriolecta
Tested Number: 2
Total Sample Time: 5 sec.

| Number | D-A | V-A | A-AC | Number | D-A | V-A | A-AC |
|---|---|---|---|---|---|---|---|
| 1 | 150 | 0.00 | 0.00 | 31 | 160 | 0.00 | 0.00 |
| 2 | 200 | 600.00 | 0.00 | 32 | 250 | 1080.00 | 12960.00 |
| 3 | 260 | 720.00 | 1440.00 | 33 | 280 | 360.00 | −8640.00 |
| 4 | 290 | 360.00 | −4320.00 | 34 | 310 | 360.00 | 0.00 |
| 5 | 290 | 0.00 | −4320.00 | 35 | 300 | −120.00 | −2880.00 |
| 6 | 340 | 600.00 | 7200.00 | 36 | 310 | 120.00 | 0.00 |
| 7 | 340 | 0.00 | −7200.00 | 37 | 340 | 360.00 | 2880.00 |

TABLE 3-continued

Tracking Rotation of a Microbe from its Dynamic Diffraction Pattern

| 8 | 50 | 840.00 | 10080.00 | 38 | 350 | 120.00 | −2880.00 |
|---|---|---|---|---|---|---|---|
| 9 | 80 | 360.00 | −5760.00 | 39 | 20 | 360.00 | 2880.00 |
| 10 | 100 | 240.00 | −1440.00 | 40 | 100 | 960.00 | 7200.00 |
| 11 | 120 | 240.00 | 0.00 | 41 | 130 | 360.00 | −7200.00 |
| 12 | 130 | 120.00 | −1440.00 | 42 | 160 | 360.00 | 0.00 |
| 13 | 150 | 240.00 | 1440.00 | 43 | 250 | 1080.00 | 8640.00 |
| 14 | 170 | 240.00 | 0.00 | 44 | 290 | 480.00 | −7200.00 |
| 15 | 200 | 360.00 | 1440.00 | 45 | 310 | 240.00 | −2880.00 |
| 16 | 270 | 840.00 | 5760.00 | 46 | 340 | 360.00 | 1440.00 |
| 17 | 290 | 240.00 | −7200.00 | 47 | 0 | 240.00 | −1440.00 |
| 18 | 320 | 360.00 | 1440.00 | 48 | 20 | 240.00 | 0.00 |
| 19 | 330 | 120.00 | −2880.00 | 49 | 60 | 480.00 | 2880.00 |
| 20 | 310 | −240.00 | 1440.00 | 50 | 110 | 600.00 | 1440.00 |
| 21 | 270 | −480.00 | 2880.00 | 51 | 120 | 120.00 | −1576.00 |
| 22 | 290 | 240.00 | −2880.00 | 52 | 120 | 0.00 | −1440.00 |
| 23 | 300 | 120.00 | −1440.00 | 53 | 160 | 480.00 | 5760.00 |
| 24 | 340 | 480.00 | 4320.00 | 54 | 170 | 120.00 | −4320.00 |
| 25 | 0 | 240.00 | −2880.00 | 55 | 260 | 1080.00 | 11520.00 |
| 26 | 100 | 1200.00 | 11520.00 | 56 | 270 | 120.00 | −11570.00 |
| 27 | 110 | 120.00 | −12960.00 | 57 | 310 | 480.00 | 4320.00 |
| 28 | 120 | 120.00 | 0.00 | 58 | 310 | 0.00 | −5760.00 |
| 29 | 160 | 480.00 | 4320.00 | 59 | 310 | 0.00 | 0.00 |
| 30 | 160 | 0.00 | −5760.00 | 60 | 350 | 480.00 | 5760.00 |

Total rotation (clockwise): −0.19 (turns - −70 (degrees)
(counter-clockwise): 4.75 (turns) - 1710 (degrees)
Net rotation during sample time: 4.56 (turns) - 1640 (degrees)
Average angle velocity (clockwise): −84.00 (degrees/sec.)
(counter-clockwise): 418.78 (degrees/sec.)
Net average angle velocity: 333.56 (degrees/sec.)
Motion Characteristic: rotation in counter-clockwise direction with a few wobble.

TABLE 4

TRACKING MOTION OF MICROBES

Test Sample: Sewage water from Lewes wastewater treatment plant (4).
Sample Time in Second: 5

| Number | DX | DY | DD | AV | A0 | A1 | A2 | A3 | A4 |
|---|---|---|---|---|---|---|---|---|---|
| 1 | 58 | 39 | 70.31 | 37.98 | −250.98 | 8.550 | −0.0499 | 0.00000 | 0.0000 |
| 2 | 11 | 19 | 22.74 | 7.53 | 160.40 | −0.439 | 0.0000 | 0.00000 | 0.0000 |
| 3 | 54 | 187 | 195.00 | 45.79 | −4309.79 | 115.079 | −0.9478 | 0.00234 | −0.0018 |
| 4 | 70 | 97 | 120.14 | 30.70 | 100.50 | −1.417 | 0.0000 | 0.00000 | 0.0000 |
| 5 | 11 | 35 | 37.00 | 9.92 | 57.46 | 0.550 | 0.0000 | 0.00000 | 0.0000 |
| 6 | 23 | 152 | 153.89 | 39.88 | 3636.08 | −86.217 | 0.5135 | −0.55697 | 0.0000 |
| 7 | 58 | 195 | 203.59 | 42.28 | 21172.25 | −2258.426 | 89.5645 | −1.56458 | 0.0102 |

| RD | D0 | T0 | D1 | T1 | D2 | T2 | D3 | T3 |
|---|---|---|---|---|---|---|---|---|
| 158.99 | 7.800 | 0.000 | 7.800 | 0.000 | 7.800 | 0.000 | 7.800 | 0.000 |
| 29.51 | 7.800 | 0.000 | 7.800 | 0.000 | 5.514 | −45.000 | 8.72 | 63.435 |
| 8277.41 | 42.003 | 68.199 | 8.720 | 26.565 | 11.029 | −45.000 | 8.720 | 26.565 |
| 97.90 | 14.063 | −33.690 | 14.063 | −33.690 | 11.029 | −45.000 | 7.800 | 0.000 |
| 98.70 | 7.800 | 0.000 | 8.720 | 63.435 | 8.720 | −26.565 | 5.514 | 56.000 |
| 1762.22 | 14.063 | −56.310 | 14.063 | 56.310 | 11.029 | −45.000 | 17.440 | 63.435 |
| 4274.60 | 22.740 | 59.036 | 24.972 | 51.340 | 22.741 | 59.036 | 21.002 | 68.199 |

| D4 | T4 | D5 | T5 | D6 | T6 | D7 | T7 | D8 |
|---|---|---|---|---|---|---|---|---|
| 5.514 | 45.000 | 7.800 | 0.000 | 8.720 | −26.565 | 14.063 | 33.690 | 8.720 |
| 7.800 | 0.000 | 0.000 | 0.000 | 0.000 | 0.000 | 0.000 | 0.000 | 0.000 |
| 22.062 | −45.000 | 15.600 | 0.000 | 11.029 | −45.000 | 11.029 | 45.000 | 11.700 |
| 17.441 | −63.435 | 11.029 | −45.000 | 8.720 | −26.565 | 17.441 | −63.435 | 8.720 |
| 5.515 | 45.000 | 7.800 | 0.000 | 5.515 | 45.000 | 0.000 | 0.000 | 0.000 |
| 11.7700 | 0.000 | 8.720 | −26.565 | 11.029 | 45.000 | 19.886 | 78.690 | 16.080 |
| 28.392 | 74.055 | 11.700 | 0.000 | 11.7700 | 0.000 | 28.392 | −74.055 | 19.886 |

| T8 | D9 | T9 | D10 | T10 | D11 | T11 | D12 | T12 |
|---|---|---|---|---|---|---|---|---|
| −26.565 | 7.800 | 0.000 | 8.720 | −26.565 | 8.720 | 63.435 | 36.793 | −57.995 |
| 0.000 | 0.000 | 0.000 | 0.000 | 0.000 | 0.000 | 0.000 | 0.000 | 0.000 |
| 0.000 | 11.700 | 0.000 | 21.002 | −68.199 | 12.332 | 71.565 | 21.002 | −68.199 |
| 26.565 | 11.029 | −45.000 | 11.029 | 45.000 | 15.600 | 0.000 | 5.515 | 45.000 |
| 0.000 | 0.000 | 0.000 | 0.000 | 0.000 | 0.000 | 0.000 | 0.000 | 0.000 |
| 75.964 | 21.002 | 68.199 | 19.500 | 0.000 | 8.720 | 0.000 | 26.161 | 0.000 |

TABLE 4-continued
TRACKING MOTION OF MICROBES

| | | | | | | | | |
|---|---|---|---|---|---|---|---|---|
| −78.690 | 19.886 | 78.690 | 0.000 | 0.000 | 0.000 | 0.000 | 0.000 | 0.000 |

Notes:
Number - represents number of microbes to be tracked.
DX,DY - maximum position change in X and Y direction (in micron).
DD - maximum linear position change (in micron).
AV - average velocity during sample period (micron/sec).
A0 to A4 - zero to forth order coefficient of motion trace equation.
RD - mean error of the least square curve fitting.
D0 to T12 - moving distance at each subsection during ST (in micron).
T0 to T12 - moving direction (arctan) of each subsection (in angle).

We claim:

1. A system for monitoring microbe form and activity in a fluid sample comprising:
   a laser station;
   a sample collector section;
   a picture taking station; and
   a monitor station; said sample collection station being adapted to hold the fluid sample, laser emitting means in said laser station for directing a laser beam at the fluid sample in said sample collector station with the beam being diffracted by microorganisms in the sample and to said picture taking station, picture taking means in said picture taking station for taking a picture of the activity in the sample in accordance with the diffracted beam, a photodetector for monitoring Doppler shifted frequencies and monitor means in said monitor station for converting said picture to an analyzable record of the activity.

2. A system for monitoring life in fluids as claimed in claim 1 wherein said picture taking means is a camera.

3. A system for monitoring life in fluids as claimed in claim 1 wherein said picture taking means is a video camera.

4. A system for monitoring microbe activity as claimed in claim 1, wherein said monitor means is a VCR.

5. A system for monitoring microbe activity as claimed in claim 1, wherein said monitor means consist of a VCR and a Television.

6. A system for monitoring microbe activity as claimed in claim 1, wherein said monitor means consist of a frame grabber, a computer and a monitor.

7. A system for monitoring microbe activity in a fluid as claimed in claim 1, wherein said sample collector station comprises a holder and said holder is adapted to an interrupted flow system.

8. A system for monitoring microbe activity as claimed in claim 1, further comprising of at least one lens station before said sample collector directing said laser beam for said laser station to said sample collector station.

9. A system for monitoring microbe activity in a fluid as claimed in claim 1, wherein said laser station comprises a helium neon laser.

10. A system for monitoring microbe activity in a fluid as claimed in claim 1, wherein said laser station comprises a solid state laser diodes.

11. A system for monitoring microbe activity as claimed in claim 1, wherein said sample collector station allows free exchange of dissolved gasses with the surrounding air.

12. A system for monitoring microbe activity in a fluid as claimed in claim 11, wherein said sample collector station comprises a holder and said holder is made of glass.

13. A system for monitoring microbe activity in a fluid as claimed in claim 1, further comprising a laser beam splitter.

14. A system for monitoring microbe activity in a fluid as claimed in claim 13, wherein the system has two independent laser beams.

15. A system for monitoring microbe activity as claimed in claim 1, further comprising a blocker slide between said sample collection station and said picture taking station for blocking out of a selected portion the undiffracted laser beam.

16. A system for monitoring microbe activity as claimed in claim 15, wherein said monitor means consist of a VCR and a Television.

17. A system for monitoring microbe activity as claimed in claim 15, wherein said monitor means consist of a frame grabber, a computer and a monitor.

18. A method for monitoring microbe activity in a fluid sample comprising:
   emitting a laser beam from a laser,
   scattering or diffracting the laser light from bodies in the fluid sample in accordance with microbe activity,
   taking a picture of the microbe activity in the sample from the beam diffracted from the sample, and
   monitoring the picture to monitor the microbe activity,
   wherein said fluid sample is selected from the group consisting of blood, water, industrial process fluid and beverage, and
   including a step of comparing the microbe activity in the picture with a reference standard.

19. A method for monitoring microbe activity as claimed in claim 18, including the step of blocking a portion of the laser beam after the beam has been passed through the sample and before the picture is taken.

20. A method for monitoring microbe activity as claimed in claim 18, wherein the monitoring consists of a VCR and a Television.

21. A method for monitoring microbe activity as claimed in claim 18, wherein said monitoring consists of a frame grabber, a computer and a monitor.

22. A method for monitoring microbe activity as claimed in claim 18, wherein the taking a picture is by a camera.

23. A method for monitoring microbe activity as claimed in claim 18, wherein the taking a picture is by a video camera.

24. A method for monitoring microbe activity as claimed in claim 18, wherein the monitoring consists using a VCR.

25. A method for monitoring microbe activity as claimed in claim 18, wherein the fluid sample is waste water in a sewage disposal plant, and including the step of comparing the microbe activity in the picture with a reference standard.

26. A method for monitoring microbe activity as claimed in claim 18, wherein additional information given by Doppler shifted frequencies is gathered together and monitored.

27. A method for monitoring microbe activity as claimed in claim 18, wherein the fluid sample is blood, and including the step of comparing the microbe activity in the picture with a reference standard.

28. A method for monitoring microbe activity as claimed in claim 18, wherein the fluid sample is a beverage, and including the step of comparing the microbe activity in the picture with a reference standard.

29. A method for monitoring microbe activity as claimed in claim 18, wherein the fluid sample is an industrial process fluid, and including the step of comparing the microbe activity in the picture with a reference standard.

30. A method for monitoring microbe activity as claimed in claim 18, wherein the sample flows through a transparent vessel, stopping the flow for a period of examination, restarting the flow and intermittently restarting the flow during corresponding periods of examination.

31. A method for monitoring microbe activity as claimed in claim 18, wherein means are provided for maintaining the image of the microbe in a preferred position on a monitor screen.

32. A method for monitoring microbe activity as claimed in claim 18, wherein the microbe is a parasite.

33. A method for monitoring microbe activity as claimed in claim 32, wherein the parasite is a giardia parasite.

* * * * *

UNITED STATES PATENT AND TRADEMARK OFFICE
CERTIFICATE OF CORRECTION

PATENT NO. : 5,229,849
DATED : July 20, 1993
INVENTOR(S) : Pleass, et. al.

It is certified that error appears in the above-indentified patent and that said Letters Patent is hereby corrected as shown below:

In Column 1, after the Title, please insert the following phrase:

--This invention was made with government support under NIH Grant No. 42012 awarded by the National Institutes of Health. The government has certain rights in the invention.--

Signed and Sealed this

Thirteenth Day of December, 1994

Attest:

BRUCE LEHMAN

Attesting Officer

Commissioner of Patents and Trademarks